US00PP15501P3

(12) United States Plant Patent
Meilland

(10) Patent No.: US PP15,501 P3
(45) Date of Patent: Jan. 25, 2005

(54) *FLORIBUNDA* ROSE PLANT NAMED 'MEIMANESK'

(50) Latin Name: *Rosa hybrida*
Varietal Denomination: Meimanesk

(75) Inventor: Alain A. Meilland, Antibes (FR)

(73) Assignee: Meilland International S.A., Le Luc (FR)

( * ) Notice: Subject to any disclaimer, the term of this patent is extended or adjusted under 35 U.S.C. 154(b) by 16 days.

(21) Appl. No.: 10/650,700

(22) Filed: Aug. 29, 2003

(65) Prior Publication Data

US 2004/0158896 P1 Aug. 12, 2004

(51) Int. Cl.[7] ..... A01H 5/00
(52) U.S. Cl. ..... Plt./148
(58) Field of Search ..... Plt./141, 148, 102, Plt./107

(56) References Cited

U.S. PATENT DOCUMENTS

PP8,114 P * 1/1993 Ilsink ..... Plt./150

* cited by examiner

*Primary Examiner*—Anne Marie Grunberg
*Assistant Examiner*—June Hwu
(74) *Attorney, Agent, or Firm*—Burns, Doane, Swecker & Mathis, L.L.P.

(57) ABSTRACT

A new and distinct variety of *Floribunda* rose plant is provided which abundantly forms on a nearly continuous basis attractive very double blossoms that are medium pink tinted with green in coloration and possess an old rose configuration. The medium green foliage contrasts nicely with the pink blossom coloration. The new variety is particularly well suited for the production of exceptionally long lasting cut flowers under greenhouse growing conditions. The plant exhibits a semi-erect growth habit, and good resistance to Botrytis and Powdery Mildew under standard greenhouse growing conditions.

1 Drawing Sheet

Figures 1, 2, 3, 4, 5, 6, 7, 8, 9, 10, 11, 12, 13, 14, 15, 16:
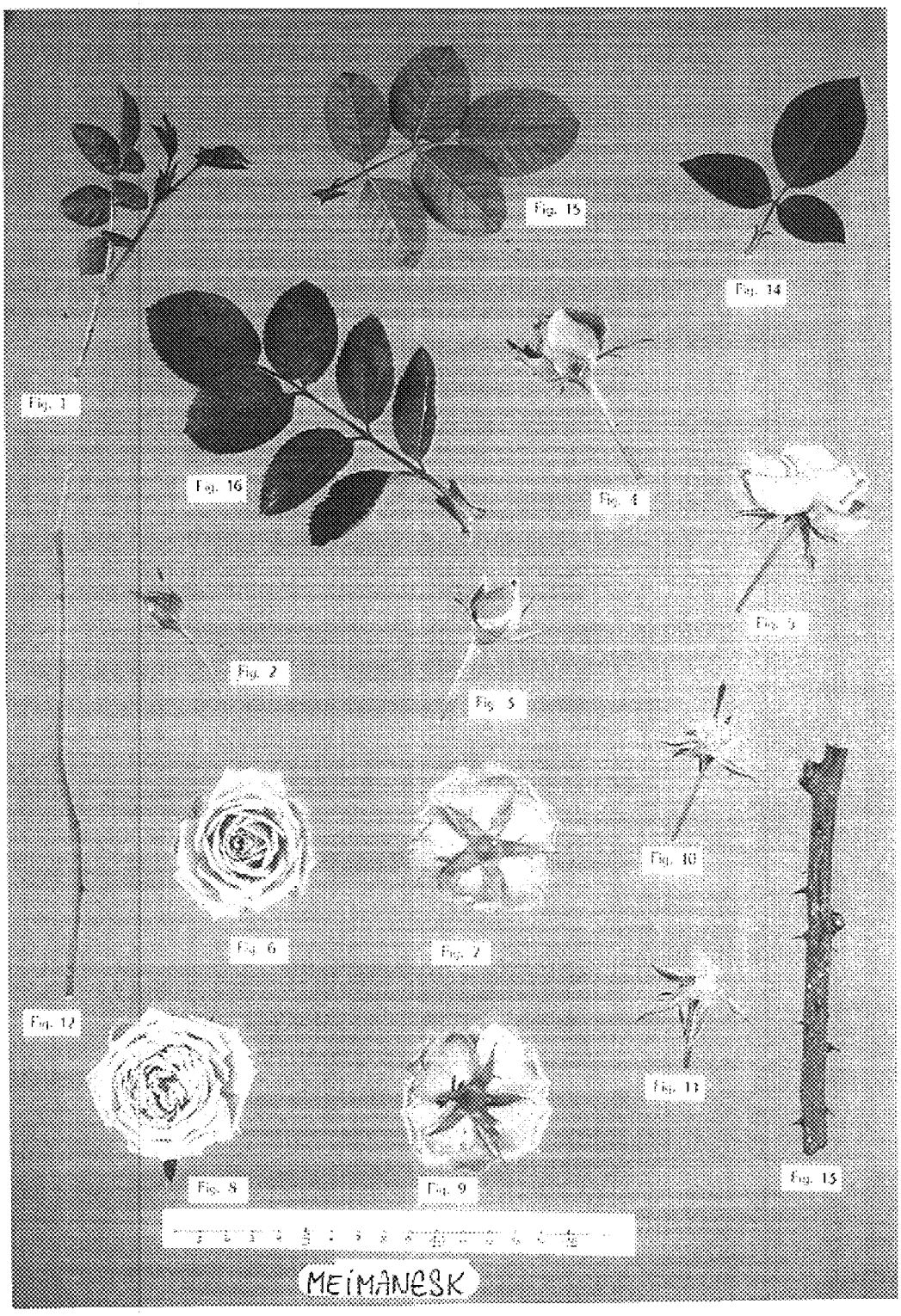

Botanical/commercial classification: *Rosa hybrida/Floribunda* Rose Plant.
Varietal denomination: cv. 'Meimanesk'.

SUMMARY OF THE INVENTION

The new variety of *Rosa hybrida Floribunda* rose plant was created by artificial pollination wherein two parents were crossed which previously had been studied in the hope that they would contribute the desired characteristics. The female parent (i.e., the seed parent) was the product of the cross at the 'Interniki' variety (U.S. Plant Pat. No. 8,114) and the 'Meinecta' variety (non-patented in the United States). The male parent (i.e., the pollen parent) was the 'Meiquiza' variety (non-patented in the United States). The parentage of the new variety can be summarized as follows:

('Interniki'×'Meinecta')×'Meiquiza'.

The seeds resulting from the above pollination were sown and small plants were obtained which were physically and biologically different from each other. Selective study resulted in the identification of a single plant of the new variety.

It was found that the new *Floribunda* rose variety of the present invention (a) exhibits a semi-erect growth habit, (b) abundantly forms attractive very double medium pink tinted with green blossoms of the old rose type, (c) is particularly well suited for cut flower production under greenhouse growing conditions, and (d) displays flowers of an exceptionally long life when cut and placed in a vase.

The new variety well meets the needs of the horticultural industry and can be used to advantage for the commercial production of cut flowers under standard under glass cultural conditions.

The new variety of the present invention can be readily distinguished from its ancestors. For instance, the flowers of the new variety possess an old rose configuration with a substantial number of petals as illustrated. The petals of the 'Interniki' variety commonly number approximately 35 to 40 and are medium red in coloration. The 'Meinecta' variety forms conical-shaped buds and its spray flowers are smaller, and pale ocher in coloration. The 'Meiquiza' variety also forms conical-shaped buds and its flowers are smaller, pale pink in coloration, and possess a classical cut flower configuration. The new variety forms globular shaped buds and flowers having an old rose configuration.

Also, the new variety of the present invention can be readily distinguished from the 'Meiptipier' variety (U.S. Plant Pat. No. 14,194) which possesses approximately 27 to 40 petals on average wherein the central petals are deep rosy pink and the outer petals are pale ivory pink with approximately 5 to 11 small petaloids being present per bloom.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meimanesk' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during September while budded on *Rosa indica* understock and growing in greenhouses at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface, and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of two year-old plants during August while budded on *Rosa indica* understock and growing in a greenhouse at Le Cannet des Maures, Var, France.

Class: *Floribunda.*

Plant:

*Height.*—Approximately 130 cm on average.

*Width.*—Approximately 30 to 40 cm on average.

*Habit.*—Semi-erect.

Branches:

*Stems.*—Surface texture: smooth and rigid. Color: near Yellow-Green Group 144A and 144B when immature, and near Yellow-Green Group 146A when mature.

*Thorns.*—Size: variable (as illustrated). Quantity: on 15 cm of young stems approximately 1 on average greater than 5 mm in length and approximately 17 on average less than 5 mm in length. Configuration: relatively straight on the upper surface and concave on the under surface. Color: immature thorns are near Yellow-Green Group 151A tinted with Greyed-Orange Group 172B, and the mature thorns are near Yellow-Green Group 151A.

Leaves:

*Stipules.*—Adnate, pectinate, broad, approximately 1.3 cm in length on average, approximately 1 cm in width on average, and near Green Group 137A in coloration.

*Petioles.*—Upper surface: glandular, smooth, medium green, near Green Group 137B and 137C. Under surface: smooth, and commonly bear a few prickles. Length: approximately 1.5 cm on average with the terminal leaflet.

*Leaflets.*—Number: 3, 5 (most often), and 7. Shape: somewhat ovate with an obtuse base and a cuspidate tip. Size: terminal leaflets commonly measure approximately 3.5 cm in length and approximately 3 cm in width on average. Serration: simple and regular (as illustrated). General appearance: rather dense, and medium green with a dull aspect. Color (young foliage): Upper surface: near Green Group 137A with Greyed-Red Group 178A. Under surface: near Yellow-Green Group 147B and 147C with Greyed-Red Group 178A. Color (mature foliage): Upper surface: near Green Group 137A. Under surface: near Yellow-Green Group 147B and 147C.

Inflorescence:

*Number of flowers.*—Commonly in clusters of 2 to 7 flowers per stem.

*Peduncle.*—Hairy with tiny prickles, the length is approximately 5 cm on average, the diameter is approximately 0.2 cm, and the coloration is Yellow-Green Group 144B, 144C, and 144D.

*Sepals.*—Configuration: elongated, approximately 2 to 2.4 cm in length on average, tomentose on the upper surface, glandular on the under surface, two sepals commonly possess no extensions, and three sepals commonly possess weak extensions, and the coloration is near Yellow-Green Group 144A on the upper surface and near Yellow-Green Group 144D at the central area of the under surface.

*Buds.*—Shape: globular. Size: small (as illustrated). Length: approximately 2 cm on average. Color: Upper surface: as the calyx breaks near Orange Group 27A and 27B suffused and veined with Yellow-Green Group 145A together with a major suffusion of Yellow-Green Group 145A. Under surface: near Orange Group 27A and 27B broadly suffused Red Group 48D and veined with Yellow-Green Group 145A together with a major suffusion of Yellow-Green Group 145A.

*Flower.*—Shape: old rose type. Size: approximately 6 to 7 cm in diameter on average. Color (when blooming): medium pink tinted with green, the underside is near Orange Group 27B and 27C bordered with Yellow-Green Group 145A, and the under side near Orange Group 27A and 27B suffused with Red Group 48C and bordered with Yellow-Green Group 145A. Fragrance: none. Petal number: very double (as illustrated) and commonly with approximately 220 to 250 petals on average. Petal arrangement: imbricated. Petal shape: rounded. Petal length: approximately 4 cm on average. Petal width: approximately 3.5 cm on average. Petal texture: firm. Petal margin: undulated and reflexed. Petal apex: rounded and slightly pointed and sometimes denticulated. Petal base: obtuse. Pistil number: approximately 150 on average. Style length: approximately 0.2 to 0.8 cm on average. Style color: near Greyed-Yellow Group 160A. Stigma size: approximately 0.1 cm on average. Stamen: none observed during observation to date. Lasting quality: exceptionally long. The blossoms commonly last approximately 28 days on average on the plant, and approximately 21 days on average when cut and placed in a vase. Receptacle: smooth, approximately 0.6 cm in length on average, approximately 0.8 to 1 cm in width at the widest point on average, and funnel-shaped in longitudinal section. Hips: none observed to date under greenhouse growing conditions.

Development:

*Vegetation.*—Medium strength.

*Blooming.*—Abundant and nearly continuous.

*Resistance to diseases.*—Good under standard greenhouse growing conditions, especially with respect to Botrytis and Powdery Mildew.

*Aptitude to forcing.*—Very good.

I claim:

1. A new and distinct *Floribunda* rose plant characterized by the following combination of characteristics:

(a) exhibits a semi-erect growth habit, (b) abundantly forms attractive very double medium pink tinted with green blossoms of the old rose type, (c) is particularly well suited for cut flower production under greenhouse growing conditions, and (d) displays flowers of an exceptionally long life when cut and placed in a vase;

substantially as herein shown and described.

* * * * *

MEIMANESK

UNITED STATES PATENT AND TRADEMARK OFFICE

CERTIFICATE OF CORRECTION

PATENT NO. : PP 15,501 P3
DATED : January 25, 2005
INVENTOR(S) : Alain A. Meilland It is certified that error appears in the above-identified patent and that said Letters Patent is hereby corrected as shown below:

Title page,
Item [30], Foreign Application Priority Data, insert
-- February 11, 2003 (EP) ……...2003/0229. --

Signed and Sealed this

Twenty-eighth Day of June, 2005

JON W. DUDAS
*Director of the United States Patent and Trademark Office*